United States Patent [19]

Nakamura et al.

[11] Patent Number: 5,554,360
[45] Date of Patent: Sep. 10, 1996

[54] LOW-IRRITANT SHAMPOO COMPOSITION

[75] Inventors: Tohru Nakamura, Settsu; Yoshinori Shono, Ibaraki, both of Japan

[73] Assignee: Sumitomo Chemical Company, Limited, Osaka-fu, Japan

[21] Appl. No.: 224,565

[22] Filed: Apr. 7, 1994

[30] Foreign Application Priority Data

Apr. 16, 1993 [JP] Japan ................. 5-113735

[51] Int. Cl.⁶ .................................. A61K 7/075
[52] U.S. Cl. .................. 424/70.11; 424/70.19; 424/70.21; 424/70.22; 424/70.24; 424/70.31
[58] Field of Search .............. 424/70, 70.11, 424/70.19, 70.21, 70.22, 70.24, 70.31

[56] References Cited

U.S. PATENT DOCUMENTS

| 4,154,706 | 5/1979 | Kenkare et al. ............ 252/547 |
|---|---|---|
| 4,179,504 | 12/1979 | Lynch et al. . |
| 4,228,124 | 10/1980 | Kashihara et al. ............ 424/40 |
| 4,372,977 | 2/1983 | Lover et al. . |
| 4,490,279 | 12/1984 | Schmolka ............... 252/357 |
| 5,112,515 | 5/1992 | Buxton et al. ............ 424/70 |
| 5,292,504 | 3/1994 | Cardin et al. ............ 424/70 |

FOREIGN PATENT DOCUMENTS

| 2405709 | 5/1979 | France . |
|---|---|---|
| 2240716 | 8/1991 | United Kingdom . |
| 9000859 | 2/1990 | WIPO . |

*Primary Examiner*—Thurman K. Page
*Attorney, Agent, or Firm*—Birch, Stewart, Kolasch & Birch, LLP

[57] ABSTRACT

There is disclosed a shampoo composition including at least one particular pyrethroid compound as an active ingredient and a combination of particular nonionic surfactants. Also disclosed is a process for producing the shampoo composition.

12 Claims, No Drawings

LOW-IRRITANT SHAMPOO COMPOSITION

The present invention relates to a low-irritant shampoo composition for the treatment of pediculosis, which contains at least one kind of pyrethroid compound in a physically and chemically stable stale as an active ingredient.

In recent years, attention has been directed mainly to the occurrence of *Pediculus humanus humanus* in the group of school children on a nationwide scale. With a rapid increase in the number of passengers, there has been also found scattered occurrence of *Pediculus humanus humanus*; however, it is difficult to grasp the real state of such occurrence because its prevalence does not come to the surface, which is now becoming an object of public concern (see, e.g., Hifu-rinsho, Vol. 31, No. 7 (1989), 863–866; and J. Aichi Med. Univ. Assoc., Vol. 17, No. 5 (1989), 679–693).

The surfactant to be blended in shampoo compositions is required to have a low irritativeness against the skin and eyes.

In particular, with respect to therapeutic agents for pediculosis caused by *Pediculus humanus humanus*, which will be often applied to the infant stratum such as school children, there has been a demand for pediculicides having as low irritativeness as possible, which can be conveniently used.

Under these circumstances, the present inventors have intensively studied to obtain a low-irritant shampoo composition containing at least one kind of pyrethroid compound as an active ingredient in a physically and chemically stable state. As the result, they have found that a low-irritant shampoo composition containing the pyrethroid compound in a stable state without any deterioration of washing and foaming properties which are essential features of shampoos can be obtained by the use of selected nonionic surfactants in place of ionic surfactants, thereby completing the present invention.

Thus, the present invention provides a shampoo composition characterized in that it comprises:

(a) a combination of nonionic surfactants consisting of:
(1) an amine oxide of the general formula:

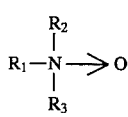

wherein $R_1$ is $C_8$–$C_{16}$ alkyl, and $R_2$ and $R_3$ are the same or different and are $C_1$–$C_2$ alkyl or hydroxyethyl;

(2) a polyoxyethylene polyoxypropylene block polymer; and (3) at least one selected from polyoxyethylene sorbitan carboxylates and polyoxyethylene alkyl phenyl ethers; and (b) at least one pyrethroid compound as an active ingredient, which is selected from the group consisting of:
3-phenoxybenzyl(1RS)-cis-trans-chrysanthemate(phenothrin);
3-phenoxybenzyl(1RS)-cis-trans-3-(2,2-dichlorovinyl)-2,2-di-methylcyclopropanecarboxylate(permethrin);
(RS)-3-allyl-2-methyl-4-oxocyclopent-2-enyl(1RS)-cis-trans-chrysanthemate(allethrin);
cyano(4-fluoro-3-phenoxyphenyl)methyl3-(2,2-dichloroethenyl)-2,2-dimethylcyclopropanecarboxylate(cyfluthrin);
(RS)-2-methyl-4-oxo-3-(2-propynyl)cyclopent-2-enyl(1RS)-cis-trans-chrysanthemate(prallethrin); and
natural pyrethrins.

It is well known that pyrethroid-type insecticides are effective for wide variety of insect pests such as imagoes of flies and mosquitos, cockroaches, fleas, house mite (*Ornithonyssus bacoi*), bedbugs and maggots, and they have advantages of being chemically stable and having a quite low toxicity against man and beasts.

Examples of the amine oxide to be used in the shampoo composition according to the present invention are alkyl dimethyl amine oxides such as lauryl dimethyl amine oxide, myristyl dimethyl amine oxide and N-coco-N,N-dimethyl amine oxide; alkyl diethyl amine oxides such as lauryl diethyl amine oxide; lauryl methyl ethyl amine oxide; and lauryl dihydroxyethyl amine oxide. Preferred are alkyl dimethyl amine oxides such as lauryl dimethyl amine oxide.

The amount of amine oxide to be used is usually in the range of 1% to 10% by weight, preferably 1.5% to 4% by weight in view of the low irritativeness and excellent physical stability, based on the total weight of the shampoo composition according to the present invention.

Particularly useful examples of the polyoxyethylene polyoxypropylene block polymer are those containing 4 to 200 units of ethyleneoxide in the polyoxyethylene portion (hereinafter referred to as "POE") and 5 to 100 units of propyleneoxide in the polyoxypropylene portion (hereinafter referred to as "POP"). Preferred are POE (160) POP (30) block polymer, POE (20) POP (20) block polymer, POE (124) POP (39) block polymer and POE (196) POP (67) block polymer.

The amount of polyoxyethylene polyoxypropylene block polymer to be used is usually in the range of 1% to 50% by weight, preferably 20% to 40% by weight, based on the total weight of the shampoo composition according to the present invention.

Preferred examples of the polyoxyethylene sorbitan carboxylate are those having a hydrophilic-lipophilic balance (HLB) of 9 or more, such as POE (20) sorbitan monolaurate, POE (20) sorbitan monopalmitate, POE (20) sorbitan monostearate, POE (20) sorbitan monooleate and POE (20) sorbitan monoisostearate.

The amount of polyoxyethylene sorbitan carboxylate to be used is usually in the range of 1% to 15% by weight, preferably 2% to 10% by weight, based on the total weight of the shampoo composition according to the present invention.

Preferred examples of the polyoxyethylene alkyl phenyl ether are those having an HLB of 9 or more, such as POE nonylphenyl ether and POE octylphenyl ether. More preferred are POE (7.5) nonylphenyl ether, POE (10) nonylphenyl ether, POE (15) nonylphenyl ether, POE (20) nonylphenyl ether and POE (30) octylphenyl ether.

The amount of polyoxyethylene alkyl phenyl ether to be used is usually in the range of 1% to 10% by weight, preferably 2% to 5% by weight, based on the total weight of the shampoo composition according to the present invention.

The pyrethroid compound to be used in the shampoo composition according to the present invention may have optical isomers, e.g., 3-phenoxybenzyl (1R)-cis-trans-chrysanthemate (d-phenothrin), (S)-2-methyl-4-oxo-3-(2-propynyl)cyclopent-2-enyl( 1R)-cis-trans-chrysanthemate(d-allethrin), cis-trans-chrysanthemate and (RS)-3-allyl-2-methyl-4-oxocyclopent-2-enyl( 1R)-cis-trans-chrysanthemate(d-allethrin). Preferred is d-phenothrin.

The amount of pyrethroid compound to be used, although it is not particularly limited so long as it is therapeutically effective, is usually in the range of 0.05% to 10% by weight, preferably 0.1% to 2% by weight, based on the total weight of the shampoo composition according to the present invention.

The shampoo composition of the present invention may further contain various conventional additives, such as water, preservatives, antimicrobials, perfumes, pigments, buffers, pH regulating agents, antioxidants, viscosity regulating agents, foam stability agents, chelating agents and conditioners, in amounts having no inhibitory effect on the excellent advantages of the shampoo composition.

Particularly effective examples of the antioxidant to be used in the shampoo composition according to the present invention are sodium edetate and dibutylhydroxytoluene.

The shampoo composition of the present invention may preferably be adjusted to a pH value around neutrality, such as in the range of 4 to 8, more preferably 5 to 7, by the addition of a pH regulating agent because the object of the present invention is to provide a shampoo composition having decreased irritativeness.

The present invention will be further illustrated by way of the following examples and experiments, which are not to be construed to limit the scope thereof.

EXAMPLE 1

| Ingredients | Amounts |
| --- | --- |
| d-Phenothrin<br>Part (A) | 0.4 g |
| Alomox ® DMCW<br>(produced by LION AKZO Ltd.;<br>containing 30% alkyl dimethyl amine oxide) | 8.0 g |
| Pluronic ® F-68<br>(produced by BASF; POE (160) POP (30)<br>block polymer) | 20.0 g |
| NIKKOL ® TO-10<br>(produced by Nikko Chemicals; POE (20)<br>sorbitan monooleate)<br>Part (B) | 5.0 g |
| Sodium edetate | 0.001 g |
| Perfume | slight |
| Hydrochloric acid | appropriate |
| Purified water to be added so as to give the<br>total volume of 100 ml | |

The ingredients of part (A) and an appropriate amount of purified water were mixed together with stirring, after which the mixture was adjusted to pH 6 by the addition of hydrochloric acid. Then, d-phenothrin and the ingredients of part (B) were added to this mixture with stirring, followed by the addition of remaining purified water, which afforded a shampoo composition.

In the same manner as described above, various shampoo compositions were prepared in the following Examples 2–6 and Comparative Examples 1–5.

EXAMPLE 2

| Ingredients | Amounts |
| --- | --- |
| d-Phenothrin<br>Part (A) | 0.4 g |
| Alomox ® DMCW (as described above) | 12.5 g |
| Pluronic ® F-68 (as described above) | 20.0 g |
| NIKKOL ® TO-10 (as described above)<br>Part (B) | 5.0 g |
| Sodium edetate | 0.001 g |
| Perfume | slight |
| Hydrochloric acid | appropriate |
| Purified water to be added so as to give the<br>total volume of 100 ml | |

EXAMPLE 3

| Ingredients | Amounts |
| --- | --- |
| d-Phenothrin<br>Part (A) | 0.4 g |
| Alomox ® DMCW (as described above) | 8.0 g |
| Pluronic ® L-44<br>(produced by BASF; POE (20) POP (20)<br>block polymer) | 40.0 g |
| NIKKOL ® NP-10<br>(produced by Nikko Chemicals; POE (20)<br>nonylphenyl ether)<br>Part (B) | 3.75 g |
| Sodium edetate | 0.001 g |
| Perfume | slight |
| Pigment | slight |
| Hydrochloric acid | appropriate |
| Purified water to be added so as to give the<br>total volume of 100 ml | |

EXAMPLE 4

| Ingredients | Amounts |
| --- | --- |
| d-Phenothrin<br>Part (A) | 0.4 g |
| Alomox ® DMCW (as described above) | 10.0 g |
| Pluronic ® L-44 (as described above) | 40.0 g |
| NIKKOL ® TS-10<br>(produced by Nikko Chemicals; POE (20)<br>sorbitan monostearate)<br>Part (B) | 7.0 g |
| Methyl parahydroxybenzoate | 0.18 g |
| Propyl parahydroxybenzoate | 0.2 g |
| Sodium edetate | 0.001 g |
| Perfume | slight |
| Pigment | slight |
| Hydrochloric acid | appropriate |
| Purified water to be added so as to give the<br>total volume of 100 ml | |

EXAMPLE 5

| Ingredients | Amounts |
| --- | --- |
| d-Phenothrin<br>Part (A) | 0.4 g |
| Alomox ® DMCW (as described above) | 9.0 g |
| Pluronic ® F-87<br>(produced by BASF; POE (124) POP (39)<br>block polymer) | 20.0 g |
| NIKKOL ® OP-30<br>(produced by Nikko Chemicals; POE (30)<br>octylphenyl ether)<br>Part (B) | 3.75 g |
| Methyl parahydroxybenzoate | 0.1 g |
| Propyl parahydroxybenzoate | 0.01 g |
| Sodium edetate | 0.2 g |
| Perfume | slight |
| Pigment | slight |
| Hydrochloric acid | appropriate |
| Purified water to be added so as to give the<br>total volume of 100 ml | |

EXAMPLE 6

| Ingredients | Amounts |
| --- | --- |
| d-Phenothrin | 0.2 g |
| Part (A) | |
| Alomox ® DMCW (as described above) | 8.0 g |
| Pluronic ® F-127 (produced by BASF; POE (196) POP (67) block polymer) | 20.0 g |
| NIKKOL ® TO-10 (as described above) | 3.0 g |
| NIKKOL ® NP-10 (as described above) | 3.0 g |
| Part (B) | |
| Methyl parahydroxybenzoate | 0.07 g |
| Propyl parahydroxybenzoate | 0.03 g |
| Dibutyl hydroxytoluene | 0.1 g |
| Perfume | slight |
| Pigment | slight |
| Hydrochloric acid | appropriate |
| Purified water to be added so as to give the total volume of 100 ml | |

Comparative Example 1

| Ingredients | Amounts |
| --- | --- |
| d-Phenothrin | 0.2 g |
| Part (A) | |
| 70% sodium lauryl ether sulfate | 20.0 g |
| Polyethylene glycol 400 | 4.0 g |
| Coconut fatty acid diethanolamide | 1.0 g |
| POE (20) nonylphenyl ether | 12.4 g |
| 50% ethoxylated lanolin | 3.0 g |
| Part (B) | |
| 2-Bromo-2-nitropropane-1,3-diol | 0.1 g |
| 2,4-Dichlorobenzylalcohol | 0.1 g |
| Dibutyl hydroxytoluene | 0.05 g |
| Hydrochloric acid | appropriate |
| Purified water to be added so as to give the total volume of 100 ml | |

Comparative Example 2

| Ingredients | Amounts |
| --- | --- |
| d-Phenothrin | 0.4 g |
| Part (A) | |
| Sodium lauryl sulfate (30% water solution) | 24.0 g |
| Coconut fatty acid diethanolamide | 3.0 g |
| Polyoxyethylene (60) hydrogenated castor oil | 5.0 g |
| Part (B) | |
| Perfume | slight |
| Hydrochloric acid | appropriate |
| Purified water to be added so as to give the total volume of 100 ml | |

Comparative Example 3

| Ingredients | Amounts |
| --- | --- |
| Part (A) | |
| Alomox ® DMCW (as described above) | 8.0 g |
| Pluronic ® F-68 (as described above) | 20.0 g |
| NIKKOL ® TO-10 (as described above) | 5.0 g |

| Ingredients | Amounts |
| --- | --- |
| Part (B) | |
| Sodium edetate | 0.001 g |
| Perfume | slight |
| Hydrochloric acid | appropriate |
| Purified water to be added so as to give the total volume of 100 ml | |

Comparative Example 4

| Ingredients | Amounts |
| --- | --- |
| d-Phenothrin | 0.4 g |
| Part (A) | |
| Sodium lauryl sulfate (30% water solution) | 24.0 g |
| Lauric acid diethanolamide | 3.0 g |
| Polyethylene glycol 400 | 5.0 g |
| Part (B) | |
| Methyl parahydroxybenzoate | 0.1 g |
| Propyl parahydroxybenzoate | 0.1 g |
| Perfume | slight |
| Pigment | slight |
| Hydrochloric acid | appropriate |
| Purified water to be added so as to give the total volume of 100 ml | |

Comparative Example 5

| Ingredients | Amounts |
| --- | --- |
| d-Phenothrin | 0.4 g |
| Part (A) | |
| Triethanolamine lauryl sulfate | 12.0 g |
| Coconut fatty acid diethanolamide | 4.0 g |
| 1,3-Butylene glycol | 3.0 g |
| Part (B) | |
| Methyl parahydroxybenzoate | 0.1 g |
| Propyl parahydroxybenzoate | 0.1 g |
| Perfume | slight |
| Pigment | slight |
| Hydrochloric acid | appropriate |
| Purified water to be added so as to give the total volume of 100 ml | |

Experiment 1

The shampoo compositions as prepared in Examples 1–3 and Comparative Examples 1–2 were examined by the following method.

(1) Eye irritation test of rabbit

The ocular-mucous membrane primary irritation test is usually performed by the Draize method or any modification thereof.

To examine the irritativeness, the shampoo compositions of Examples 1–3 were compared with those of Comparative Examples 1–2.

Each of the shampoo compositions was applied at a volume of 0.1 ml to the eyes of three rabbits in each group, and its irritation was rated after 24 hours on the following criteria:

TABLE 1

| Test items and criteria | Scores |
| --- | --- |
| (i) Redness of conjunctiva | |
| no redness | 0 |
| slightly redness | 2 |
| obvious redness | 4 |
| hemorrhage | 6 |
| (ii) Congestion of marginal area of iris | |
| normal | 0 |
| one quarter of marginal area | 1 |
| one half of marginal area | 2 |
| three quarters of marginal area | 3 |
| all of marginal area | 4 |
| redness, discharge, folds, miosis | 8 |
| (iii) Swelling with lids | |
| no swelling | 0 |
| any swelling above normal | 2 |
| partial eversion of the lids | 4 |
| less than half eversion of the lids | 6 |
| more than half eversion of the lids | 8 |
| (iv) Opacity of cornea | |
| A. Area: | |
| no abnormality | 0 |
| one quarter of cornea | 1 |
| one half of cornea | 2 |
| three quarters of cornea | 3 |
| whole part of cornea | 4 |
| B. Degree of opacity: | |
| no opacity | 0 |
| slightly opacity | 4 |
| opacity, details of iris clearly visible | 8 |
| opacity, no details of iris visible | 12 |
| opaque | 16 |

(2) Appearance change

Each of the shampoo compositions was kept at a temperature of either −5° C. or 50° C. for one month, after which the appearance was observed with the naked eyes.

The appearance change was evaluated on the following criteria:

−: homogenous

×: inhomogeneous

The results are shown in Table 2.

TABLE 2

| | Ex. 1 | Ex. 2 | Ex. 3 | Comp. Ex. 1 | Comp. Ex. 2 |
| --- | --- | --- | --- | --- | --- |
| Irritation test (24 hr) | 5 | 5 | 6 | 15 | 16 |
| Appearance change | | | | | |
| −5° C. × 1M | — | — | — | — | X |
| 50° C. × 1M | — | — | — | — | — |

Experiment 2

Each of 50 ml of the shampoo compositions as prepared in Example 1 and Comparative Example 3 was put into a separate 100-ml polyethylene cup. At the same time, 50 ml of tap water was put into another polyethylene cup. These cups were allowed to stand at room temperature. Ten adults of *Pediculus humanus corporis* about 8 days old after the emergence were kept on a small piece of wool cloth having a size of 2 cm×2 cm, after which the piece of wool cloth was held with a pair of tweezers and put into the test shampoo composition in the polyethylene cup, followed by immersion for 2 minutes. The piece of wool cloth was then washed thoroughly with the tap water in the polyethylene cup for 1 minute. These insects were removed from the piece of wool cloth and put into a 100-ml polyethylene cup with a piece of filter paper placed on the bottom thereof, followed by keeping the cup covered with a lid for bleeding. This cup containing the insects was placed in a room thermostated at 30° C. for 1 day, after which it was examined whether the insects were still alive or dead, and mortality (%) of the insects was determined. The experiment was performed in duplicate.

The results are shown in Table 3.

TABLE 3

| Composition | Mortality (%) |
| --- | --- |
| Example 1 | 100 |
| Comp. Ex. 3 | 15 |
| Untreated | 0 |

Experiment 3

The shampoo compositions as prepared in Examples 4–6 and Comparative Examples 4–5 were examined for their physical and chemical stability (based on the ratio of residual d-phenothrin) and pH change. The appearance change was also evaluated in the same manner as described in Experiment 1 on the following criteria:

−: homogenous

×: inhomogeneous

The results are shown in Table 4.

TABLE 4

| | Ex. 4 | Ex. 5 | Ex. 6 | Comp. Ex. 4 | Comp. Ex. 5 |
| --- | --- | --- | --- | --- | --- |
| Ratio of residual d-phenothrin (%) | | | | | |
| 40° C. × 3M | 99 | 99 | 99 | 98 | 97 |
| 50° C. × 3M | 98 | 98 | 99 | 97 | 96 |
| 60° C. × 1M | 99 | 98 | 99 | 96 | 97 |
| pH | | | | | |
| Initial value | 6.0 | 6.0 | 6.0 | 6.0 | 6.0 |
| 50° C. × 1M | 6.0 | 5.9 | 5.9 | 5.7 | 5.8 |
| Appearance change | | | | | |
| −5° C. × 1M | — | — | — | X | X |
| 50° C. × 1M | — | — | — | X | — |

According to the present invention, a low-irritant shampoo composition containing at least one pyrethroid compound in a physically and chemically stable state, which has pediculicidal activity against lice or their eggs, can be obtained.

What is claimed is that:

1. A shampoo composition comprising:
   (a) a combination of nonionic surfactants consisting of:
      (1) an amine oxide of the general formula:

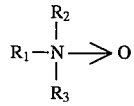

wherein $R_1$ is $C_8$–$C_{16}$ alkyl, and $R_2$ and $R_3$ are the same or different and are $C_1$–$C_2$ alkyl or hydroxyethyl;
      (2) a polyoxyethylene polyoxypropylene block polymer; and
      (3) at least one selected from polyoxyethylene sorbitan carboxylates and polyoxyethylene alkyl phenyl ethers; and
   (b) at least one pyrethroid compound as an active ingredient, which is selected from the group consisting of:
      3-phenoxybenzyl (1RS)-cis-trans-chrysanthemate(phenothrin);

3-phenoxybenzyl (1RS)-cis-trans-3-(2,2-dichlorovinyl)-2,2-dimethylcyclopropanecarboxylate(permethrin);

(RS)-3-allyl-2-methyl-4-oxocyclopent-2-enyl (1RS)-cis-trans-chrysanthemate(allethrin);

cyano(4-fluoro-3-phenoxyphenyl)methyl 3-(2,2-dichloroethenyl)-2,2-dimethylcyclopropanecarboxylate(cyfluthrin);

(RS)-2-methyl-4-oxo-3-(2-propynyl)cyclopent-2-enyl (1RS)-cis-trans-chrysanthemate(prallethrin); and natural pyrethrins.

2. A shampoo composition according to claim 1, wherein the nonionic surfactant component (3) is a polyoxyethylene sorbitan carboxylate.

3. A shampoo composition according to claim 1, wherein the nonionic surfactant component (3) is a polyoxyethylene alkyl phenyl ether.

4. A shampoo composition according to claim 1, wherein the pyrethroid compound is 3-phenoxybenzyl (1R)-cis-trans-chrysanthemate(d-phenothrin).

5. A shampoo composition according to claim 2, wherein the pyrethroid compound is 3-phenoxybenzyl (1R)-cis-trans-chrysanthemate(d-phenothrin).

6. A shampoo composition according to claim 3, wherein the pyrethroid compound is 3-phenoxybenzyl (1R)-cis-trans-chrysanthemate(d-phenothrin).

7. A process for producing a shampoo composition according to claim 1, which comprises mixing (a) a combination of nonionic surfactants consisting of:

(1) an amine oxide of the general formula:

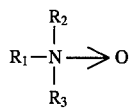

wherein $R_1$ is $C_8$–$C_{16}$ alkyl, and $R_2$ and $R_3$ are the same or different and are $C_1$–$C_2$ alkyl or hydroxyethyl;

(2) a polyoxyethylene polyoxypropylene block polymer; and (3) at least one selected from polyoxyethylene sorbitan carboxylates and polyoxyethylene alkyl phenyl ethers; and (b) at least one pyrethroid compound as an active ingredient, which is selected from the group consisting of:

3-phenoxybenzyl (1RS)-cis-trans-chrysanthemate(phenothrin);

3-phenoxybenzyl (1RS)-cis-trans-3-(2,2-dichlorovinyl)-2,2-dimethylcyclopropanecarboxylate(permethrin);

(RS)-3-allyl-2-methyl-4-oxocyclopent-2-enyl (1RS)-cis-trans-chrysanthemate(allethrin);

cyano(4-fluoro-3-phenoxyphenyl)methyl 3-(2,2-dichloroethenyl)-2,2-dimethylcyclopropanecarboxylate(cyfluthrin);

(RS)-2-methyl-4-oxo-3-(2-propynyl)cyclopent-2-enyl (1 RS)-cis-trans-chrysanthemate(prallethrin); and natural pyrethrins.

8. A shampoo composition according to claim 1, wherein the amount of the amine oxide is 1% to 10% by weight, based on the total weight of the shampoo composition.

9. A shampoo composition according to claim 1, wherein the amount of the polyoxyethylene polyoxypropylene block polymer is 1% to 50% by weight, based on the total weight of the shampoo composition.

10. A shampoo composition according to claim 1, wherein the amount of the polyoxyethylene sorbitan carboxylate is 1% to 15% by weight, based on the total weight of the shampoo composition.

11. A shampoo composition according to claim 1, wherein the amount of the polyoxyethylene alkyl phenyl ether is 1% to 10% by weight, based on the total weight of the shampoo composition.

12. A shampoo composition according to claim 1, wherein the amount of the pyrethroid compound is 0.05% to 10% by weight, based on the total weight of the shampoo composition.

* * * * *